United States Patent [19]

Tenney

[11] Patent Number: 4,512,515
[45] Date of Patent: Apr. 23, 1985

[54] THERMAL FOG GENERATOR

[75] Inventor: William L. Tenney, Crystal Bay, Minn.

[73] Assignee: London Fog, Inc., Long Lake, Minn.

[21] Appl. No.: 502,505

[22] Filed: Jun. 9, 1983

[51] Int. Cl.³ .............................................. A01M 7/00
[52] U.S. Cl. ..................................... 239/129; 239/373
[58] Field of Search ............... 239/129, 135, 152, 153, 239/154, 339, 340, 343, 353, 370, 375, 373; 252/359 A

[56] References Cited

U.S. PATENT DOCUMENTS

| | | | |
|---|---|---|---|
| 2,896,855 | 7/1959 | Neville | 239/129 |
| 2,901,182 | 8/1959 | Cragg et al. | 239/129 |
| 3,205,176 | 9/1965 | Tenney | 252/359 |
| 3,244,641 | 4/1966 | Durr et al. | 239/129 |
| 3,607,780 | 9/1971 | Scott | 252/359 A |
| 3,646,701 | 3/1972 | Pfaffenbach | 252/359 A |
| 4,155,249 | 5/1979 | Scott | 73/40.7 |

FOREIGN PATENT DOCUMENTS 641739  8/1950  United Kingdom ............... 239/135

OTHER PUBLICATIONS

Turb-A-Fog Tear Gas & Smoke Generator, M-30, Scott Engineering, Auburn, Indiana.
Turb-A-Fog Thermal-Aerosol Smoke Generator, M-35, Scott Engineering, Auburn, Indiana.
Turb-A-Fog Insecticidal Fogging Equipment, Scott Engineering, Auburn, Indiana.
Owners Manual-Village Blacksmith-Engine Powered Portable Insect Killing Fogger, 1969, Village Blacksmith Division, McGraw-Edison Company.
Echo Power Blower Operator's Manual, PB-200, Kioritz Corporation, Tokyo, Japan.

Primary Examiner—Andres Kashnikow
Assistant Examiner—James R. Moon, Jr.

[57] ABSTRACT

A thermal fog generator having an internal combustion engine rotating a blower to discharge a continuous stream of air through a tube into the atmosphere. The hot exhaust gas from the engine is directed to an enclosed muffler and exhaust pipe into the air moving through the tube. A liquid formulation stored in a container is delivered to the muffler. The hot exhaust gas in the muffler atomizes and vaporizes the liquid formulation and carries the atomized and vaporized liquid formulation to the air moving in the tube. The cool air condenses the vaporized liquid formulation to produce a fog. A hand-operated control is used to regulate the supply of engine crankcase gases under pressure derived from the engine crankcase to the container. The control includes a valve unit operable to bypass the crankcase gases under pressure from the engine to the atmosphere and vent the gases under pressure from the container to promptly terminate the flow of liquid formulation to the muffler.

56 Claims, 10 Drawing Figures

THERMAL FOG GENERATOR

FIELD OF INVENTION

The invention relates to an apparatus, known as a thermal fog generator, having an internal combustion engine and means for supplying a liquid, such as an insecticide or CS and CN formulations, to the hot exhaust gas of the engine. The heat of the exhaust gas vaporizes the liquid. The vapor, along with the exhaust gas, is dispensed into the atmosphere where it condenses to form a fog.

BACKGROUND ART

Thermal fog generators having internal combustion engines and liquid systems for introducing liquid into the hot engine exhaust gas to produce a vapor which, when dispensed into the atmosphere, condenses to form a fog are known prior art. Examples of this type of thermal fog generator are disclosed by Tenney in U.S. Pat. No. 3,205,176 and Scott in U.S. Pat. Nos. 3,607,780 and 4,155,249. The liquid formulations are stored in tanks and pressurized containers. The liquid in the tank of Tenney cannot be conveniently and quickly changed to a second liquid as the first liquid must be used up or drained and replaced with a second liquid. The handling of the liquid can result in spillage and contact with the operator's skin, which can cause serious chemical burns and/or poisoning. Needle valves used to regulate the rate of flow of fluid to the engine exhaust pipe are not intended to control the starting and stopping of fog generation. The liquid formulation in the pressurized container of Scott continues to flow after the engine stops, unless a separate manual valve is turned off. In the event the manual valve is not turned off, liquid formulation will flow from the generator. This can cause hazards to the operator and environment.

Portable leaf blowers having small internal combustion engines driving a rotatable air blower are used to provide a continuous air stream to remove objects, trash, leaves, and the like from lawns. These blowers may be hand-held and lightweight machines, which are carried by the operator in use. These blowers have not been equipped with fog and smoke generating systems operable to dispense fogs and smoke into the atmosphere.

SUMMARY OF INVENTION

The invention relates to an apparatus for producing and dispensing fog, smoke, and the like into the atmosphere. The apparatus utilizes an internal combustion engine to produce hot exhaust gas and a supply of gas, such as air, under pressure. The hot exhaust gas generated by the engine is carried by structures, such as a muffler and a connecting pipe, to the atmosphere. A container means stores a liquid formulation used to produce the fog. A line means connects the container means with the structure that carries the hot exhaust gas from the engine. A control means is selectively operable to supply gas under pressure from the engine crankcase to the container means. When the container means is subjected to gas pressure, the liquid formulation in the container means is forced through the line means into the structure for carrying the hot exhaust gas. The velocity and heat of the exhaust gas atomize and vaporize the liquid formulation and mix the atomized and vaporized liquid formulation with the exhaust gas. The atomized and vaporized liquid formulation and exhaust gas are discharged into the atmosphere. The cool atmospheric air condenses the vaporized liquid formulation to form the fog, smoke, and the like.

The apparatus is operable to selectively dispense an intermittent or continuous stream of fog or smoke into the atmosphere. This stream is directed away from the operator and toward an intended area or target. The control for the apparatus can be operated with a single hand of the operator. The operator can conveniently manipulate the apparatus with the same single hand to direct a quick application of fog over a selected area. The liquid formulations useable with the apparatus include insecticide liquids, CN and CS liquid formulations, horticultural and agricultural formulations, odor control formulations, and the like.

The apparatus is more particularly described as having a housing with a chamber for accommodating a blower. The housing has an air inlet opening and an air discharge opening to allow the blower to move a stream of air under pressure through the housing. A tube means associated with the air discharge opening has an air passage for directing the stream of air moved by the blower away from the operator. An internal combustion engine mounted on the housing is operable to rotate the blower and produce hot exhaust gases and a supply of gas under pressure. The blower serves as the load to absorb the crankshaft power output of the engine. A muffler attached to the engine receives the hot exhaust gases. A pipe connects the muffler to the tube means to discharge the hot exhaust gases into the air flowing through the air passage. A liquid formulation stored in a container means is supplied via line means to the muffler. A handoperated control means is selectively operable to supply the gas under pressure from the engine to the container means. When the liquid formulation in the container means is subjected to the gas pressure, it is forced through the line means into the muffler. The velocity and heat of the exhaust gases in the muffler atomize and vaporize the liquid formulation and mix it with the hot exhaust gases. The atomized and vaporized liquid formulation is carried by the connecting pipe into the air moving in the air passage of the tube means. This air is a continuously moving air stream that mixes with the atomized and vaporized liquid formulation and exhaust gases and carries them into the atmosphere. The cool air blowing through the air passage of the tube means and atmospheric air condenses the vaporized liquid formulation forming fog, smoke, and the like. Any atomized, but not vaporized, liquid formulation is blown out into the atmosphere.

A mount means releasably connects the container means with the housing. The container means can be quickly removed from the mount means and replaced with a second container means storing the liquid formulation or a different liquid formulation. The replacement of the container means can be performed with the engine operating and in a manner that minimizes the spilling of the liquid formulation. Also, the use of quick change containers facilitates the use of separate containers for different fluids. This eliminates fluid contamination caused by different types of fluid formulations being used from the same container.

The control means is operable to regulate the supply of gas under pressure from the engine to the container means without stopping the engine. The liquid formulation in the container means does not come in contact with the structure of the control means, nor flow through any of the crankcase gas pressure lines connecting the valve unit of the control means with the engine and the container means. The control means does not have any seals, nor moving parts, exposed to the liquid formulation. The control means includes a handoperated trigger associated with a handle for carrying the apparatus. The trigger functions to control a valve unit that is moved to open and closed positions to regulate the supply of gas under pressure delivered to the container means. When the valve unit is moved to its closed position, the gas under pressure from the engine is directed to the container means and forces the liquid formulation out of the container means to the muffler. When the valve unit is in the open position, the gas under pressure from the engine is vented to the engine intake air filter. The back pressure of the exhaust gas in the muffler prevents further discharge of liquid formulation into the muffler, thereby promptly terminating the atomization and vaporization of liquid formulation and the dispensing of fog, smoke, or the like.

These and other objects and advantages of the apparatus to generate and dispense fog, smoke, and the like of the invention are set out in the following description of the generator of the invention.

DESCRIPTION OF PREFERRED EMBODIMENT

Figure 1:
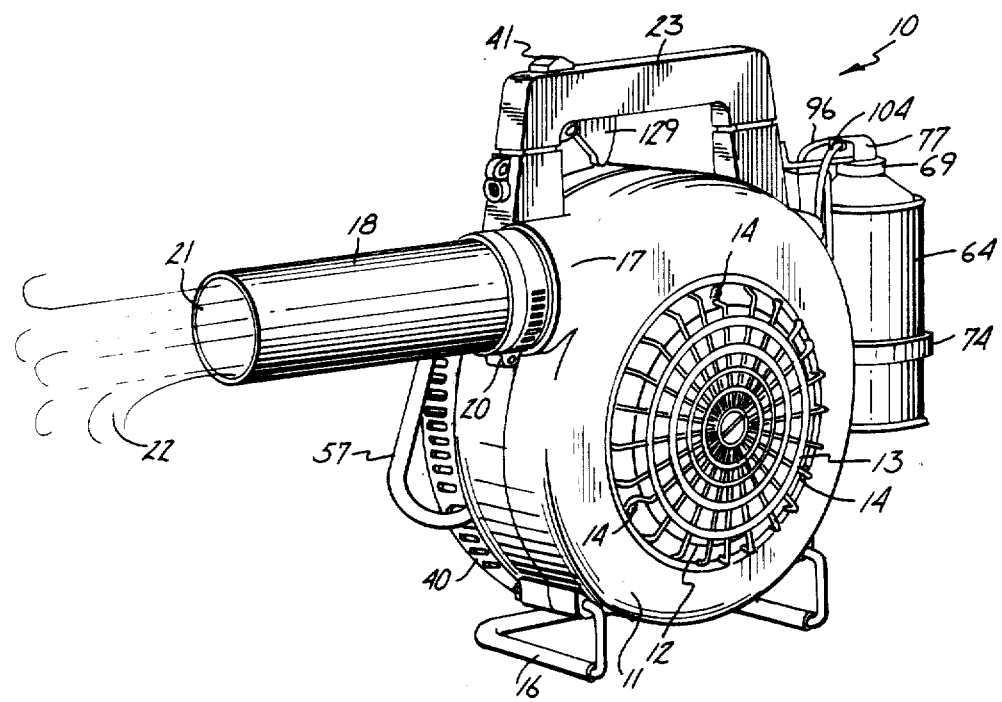
FIG. 1 is a perspective view of the thermal gas, fog, and smoke generator of the invention.
Figure 2:
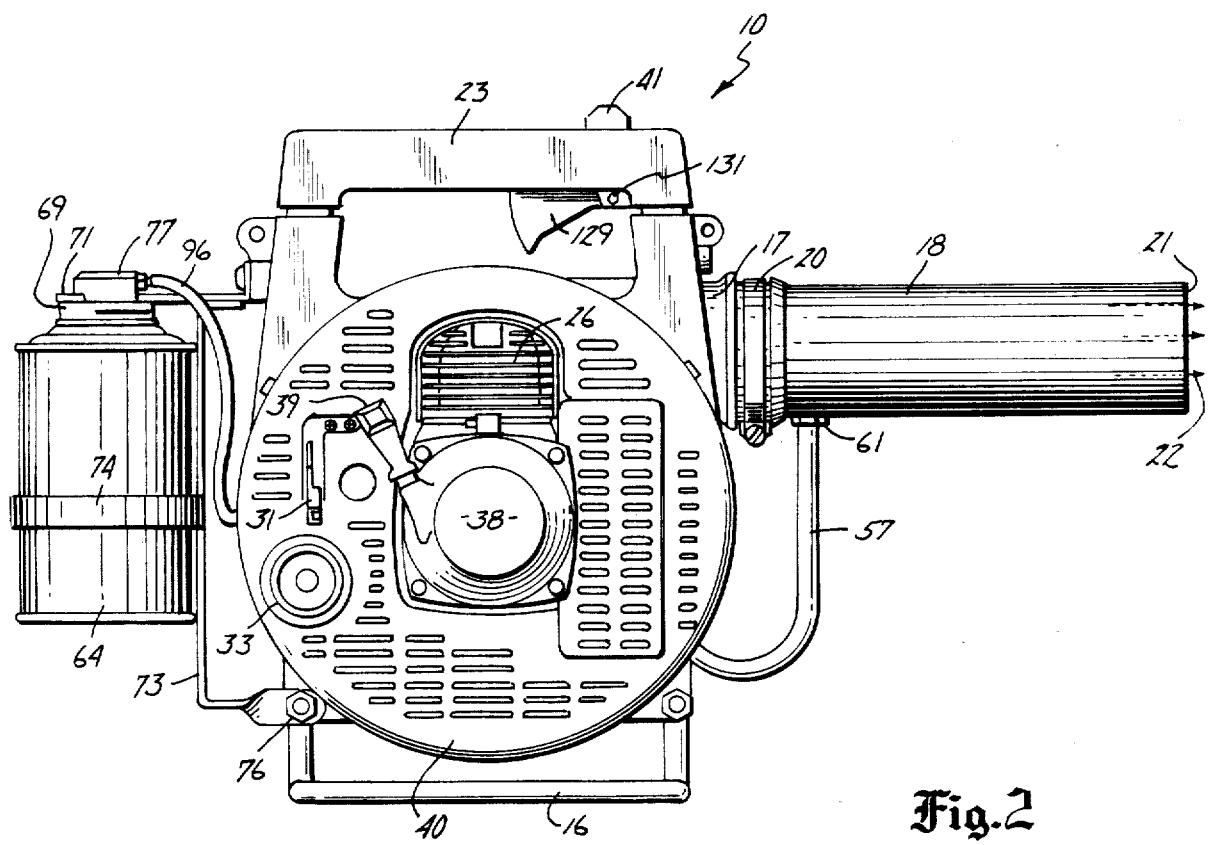
FIG. 2 is an enlarged elevational view of the engine side of the generator of FIG. 1.
Figure 3:
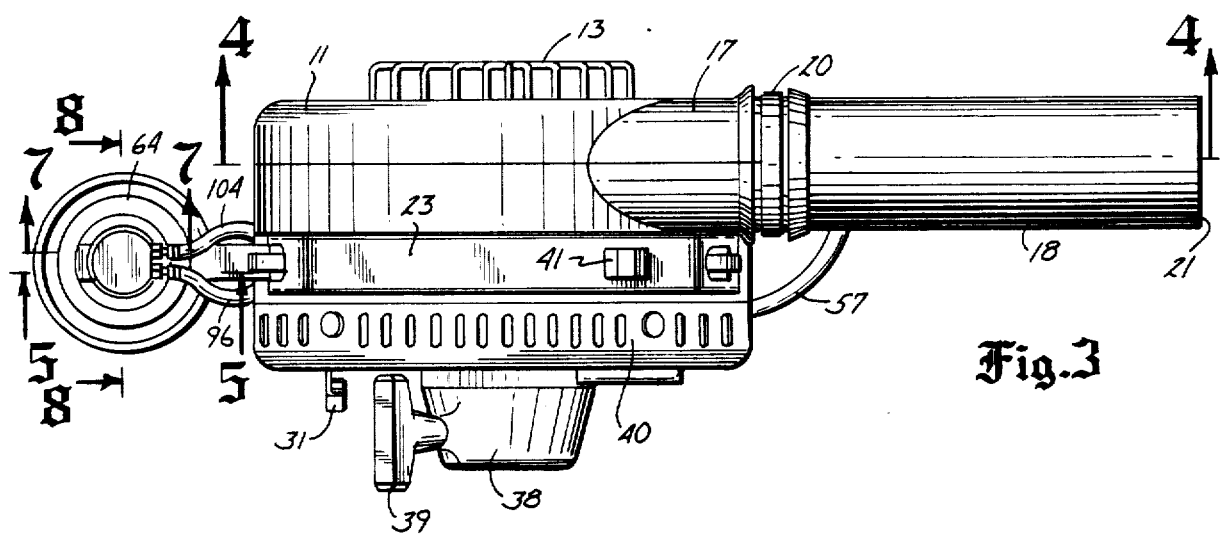
FIG. 3 is a top view of FIG. 2.

Referring to FIGS. 1, 2, and 3, there is shown a thermal gas, fog, and smoke generator of the invention indicated generally at 10 operable to disperse smoke formulations, CN and CS formulations, horticultural and agricultural formulations, odor control formulations, and the like into the atmosphere. These liquid formulations are in an atomized and vaporized state and are mixed with air and discharged with the air into the atmosphere. The vaporized liquid formulations, when introduced into cool air, condense to form aerosols consisting of microscopic particles that are suspended in the atmosphere. Non-vaporized liquids or mists are also discharged in finely atomized form into the atmosphere. The total output is commonly known as fog and smoke. Generator 10 is a lightweight portable apparatus that is hand-operated to selectively aim and direct dispersed fog away from the operator. Generator 10 operates to selectively disperse an intermittent or a continuous stream of mixture of air and fog or smoke a distance of 12 or more meters away from the operator. The entire generator 10 and its controls can be carried and operated with a single hand of the operator. The hand manipulation of generator 10 allows the operator to quickly disperse fog to a selected area away from the operator.

Apparatus 10 has a generally cylindrical housing or casing 11 provided with a circular air inlet opening 12. A circular guard 13 comprised of a plurality of radial rods is joined to circumferential concentric rings and forms an open shield over the air inlet opening 12. A plurality of screws 14 secure guard 13 to casing 11. Casing 11 is supported on a surface with a leg unit 16. The leg unit 16 functions as a stand to retain casing 11 in a generally vertical position on a support, such as the ground.

Casing 11 has a short outlet sleeve 17 extended tangentially and horizontally from the top thereof. A tube or cylindrical tube member 18 is mounted in sleeve 17 and retained therein by a clamp 20. As shown in FIGS. 4 and 9, tube 18 has a cylindrical passage 19 terminating in an open outlet end 21. As shown in FIG. 1, air, engine exhaust, atomized and condensed liquid formulation mixture 22 is discharged from outlet end 21 away from generator 10. Mixture 22 can include liquid insecticides, CN, CS, smoke formulations, horticultural and agricultural formulations, odor control, and other formulations, herein referred to as liquid formulations.

A generally inverted U-shaped handle 23 is secured to the top of casing 11. Handle 23 provides a convenient one hand grip for carrying generator 10 and supporting the controls for the operation of the generator. The operator can aim the fog generally horizontally or cause the fog to project upwardly with a single hand and with a minimum of effort. This permits the operator to aim the fog properly for delivery to the intended target area, away from the operator.

As shown in FIG. 9, casing 11 has an upright circular wall 24 supporting an internal combustion engine 26. Engine 26 is a conventional air-cooled, crankcase scavenged, two cycle internal combustion engine. Casing 11 serves as a support mount for engine 26. An all-position diaphragm carburetor 27 secured to one side of engine 26 supports an intake air filter unit 28. A choke assembly 29 is located between intake air filter unit 28 and the inlet of carburetor 27. Assembly 29 has a movable choke lever 31 operable to restrict the flow of air into carburetor 27 and thereby richen the air to fuel mixture to facilitate cold engine starting.

An arcuate-shaped fuel tank 32 having a fuel cap 33 is located below carburetor 27. A fuel line 34 connects tank 32 with carburetor 27. A bracket 35 retains fuel tank 32 in assembled relation with casing wall 24. A sparkplug 36 is installed in the cylinder head of engine 26. A high tension lead 37 connects sparkplug 36 with the spark ignition system (not shown) of the engine. The crankshaft housing of the internal combustion engine 26 supports a recoil starter unit 38 having a conventional cord and recoil starter mechanism (not shown). As shown in FIGS. 2 and 3, a handle 39 secured to the end of the cord is used as a hand grip to pull the cord out of the recoil starter unit to start internal combustion engine 26. A pan-shaped cover 40 having a plurality of slots and openings is movably mounted on the casing. Cover 40 partially closes the engine side of casing 11.

A sliding switch button 41 on the forward portion of handle 23 is used to open and close the ignition circuit for the internal combustion engine. When switch button 41 is in its forward or "run" position, the engine will start when handle 39 is pulled in an upward direction.

When switch button 41 is moved to a rearward or back position, the ignition circuit is turned off, thereby stopping engine 26.

Figure 9:
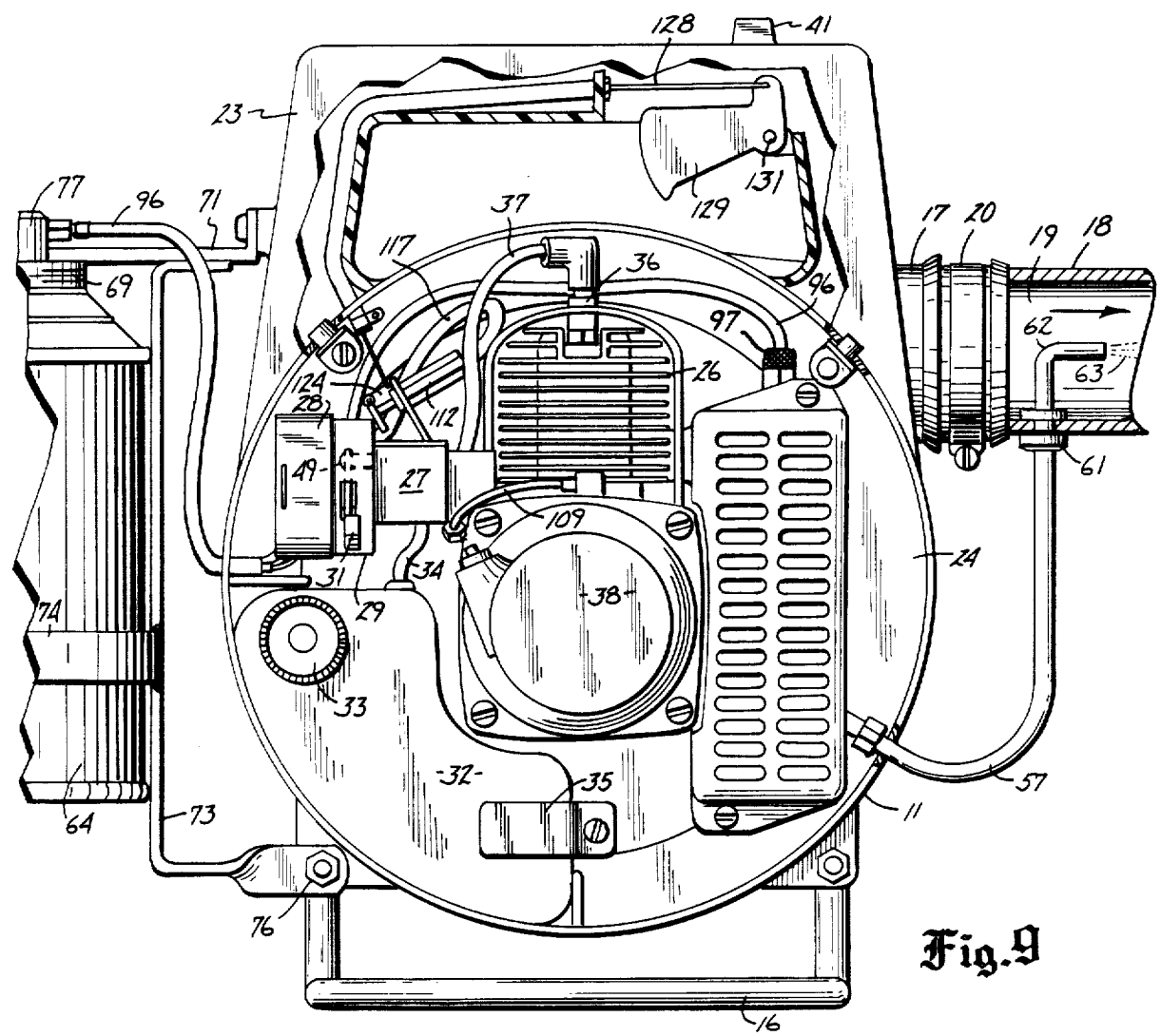
FIG. 9 is a fragmentary side elevational view, partly sectioned, of the engine side of the generator.
Figure 4:
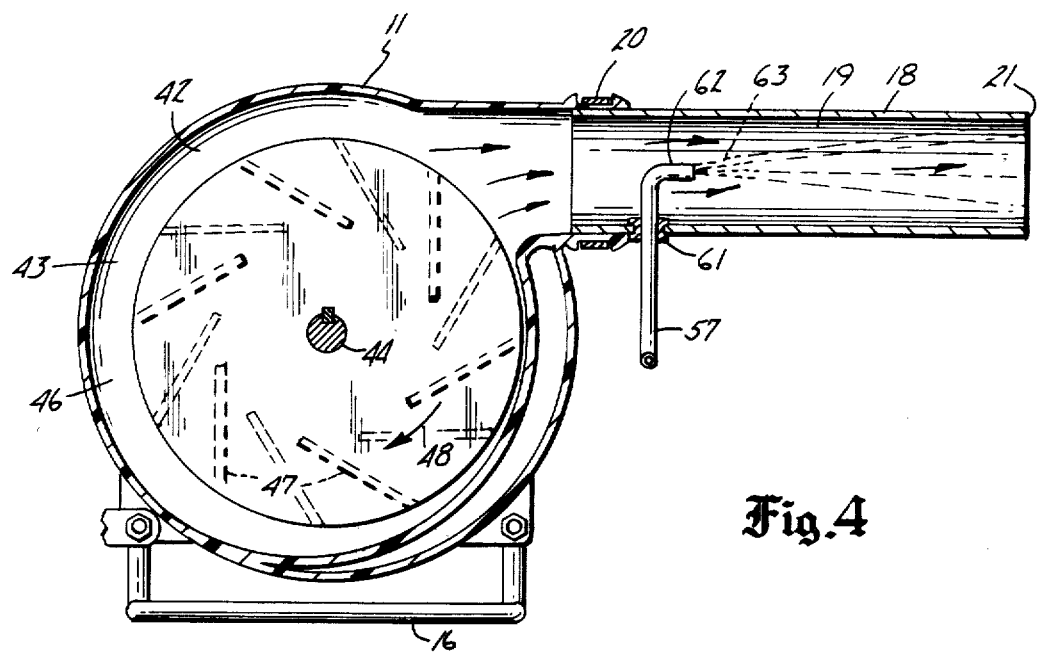
FIG. 4 is a sectional view taken along the line 4—4 of FIG. 3.
Figure 5:
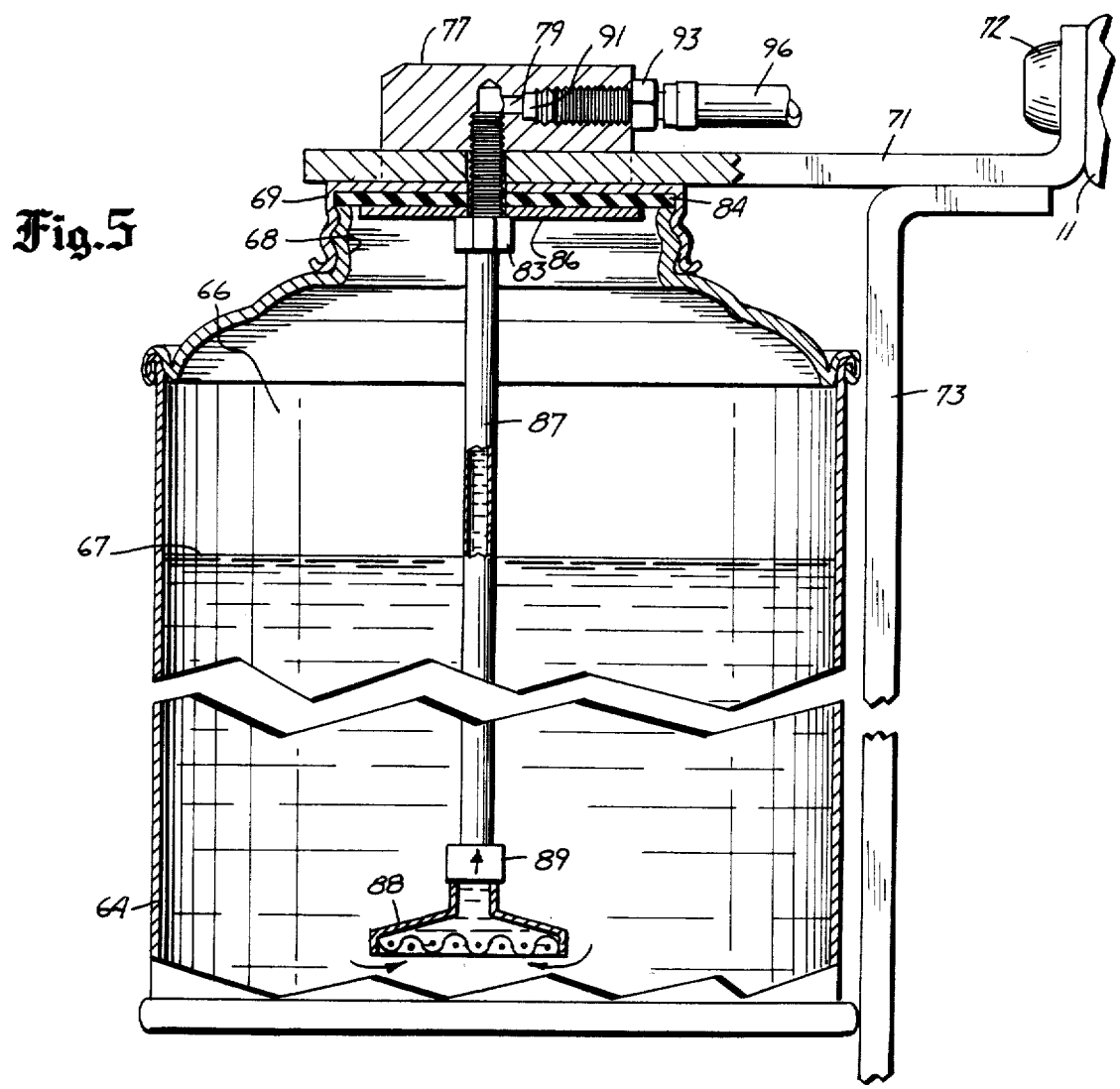
FIG. 5 is an enlarged foreshortened sectional view taken along the line 5—5 of FIG. 3.
Figure 6:
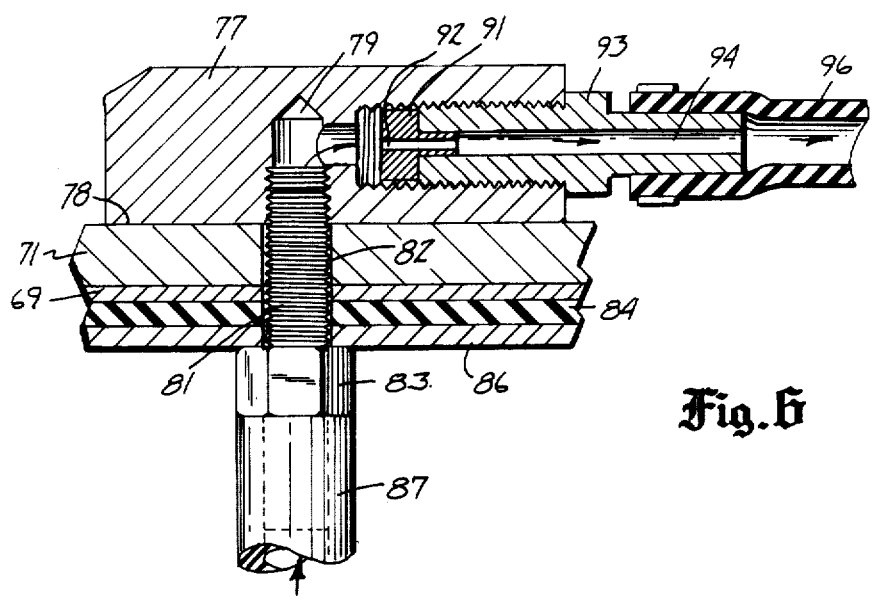
FIG. 6 is an enlarged sectional view of the cap mount of FIG. 5.
Figure 7:
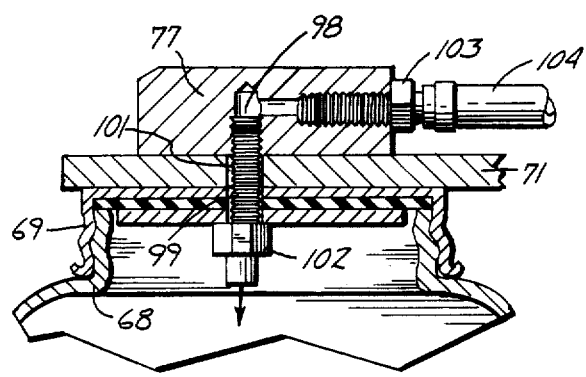
FIG. 7 is an enlarged sectional view taken along the line 7—7 of FIG. 3
Figure 8:
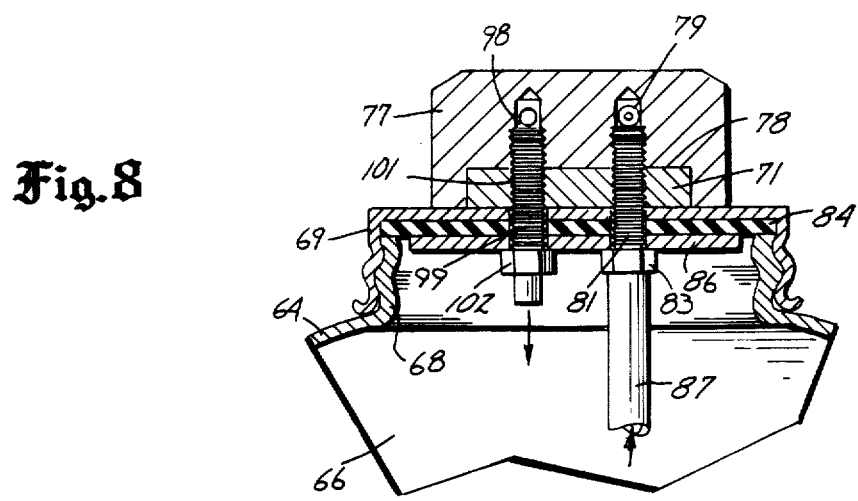
FIG. 8 is an enlarged sectional view taken along the line 8—8 of FIG. 3.

Referring to FIG. 4, casing 11 has a generally cylindrical chamber 42 accommodating a rotatable centrifugal blower rotor 43. Blower rotor 43 is mounted on crankshaft 44 of the internal combustion engine 26. Blower rotor 43 comprises a cylindrical disc 46 splined to crankshaft 44. A plurality of vanes or blades 47 are secured to the side of the disc facing inlet opening 12. The vanes or blades 47 extend generally radially along chord lines circumferentially spaced around shaft 44. Internal combustion engine 26 functions to rotate blower rotor 43 in the direction of the arrow 48. The air is moved by the rotating blower rotor 43 through inlet opening 12 of casing 11, through chamber 42, and into passage 19 of tube 18. The amount of air and the speed of the air moving through passage 19 is governed by the speed of rotation of blower rotor 43. The speed of the engine 26 and load thereon is determined by the characteristics of the blower assembly. As shown in FIG. 9, lever 31 is vertically and horizontally moved in slot 49 to control the choking for cold starting of engine 26.

Figure 10:
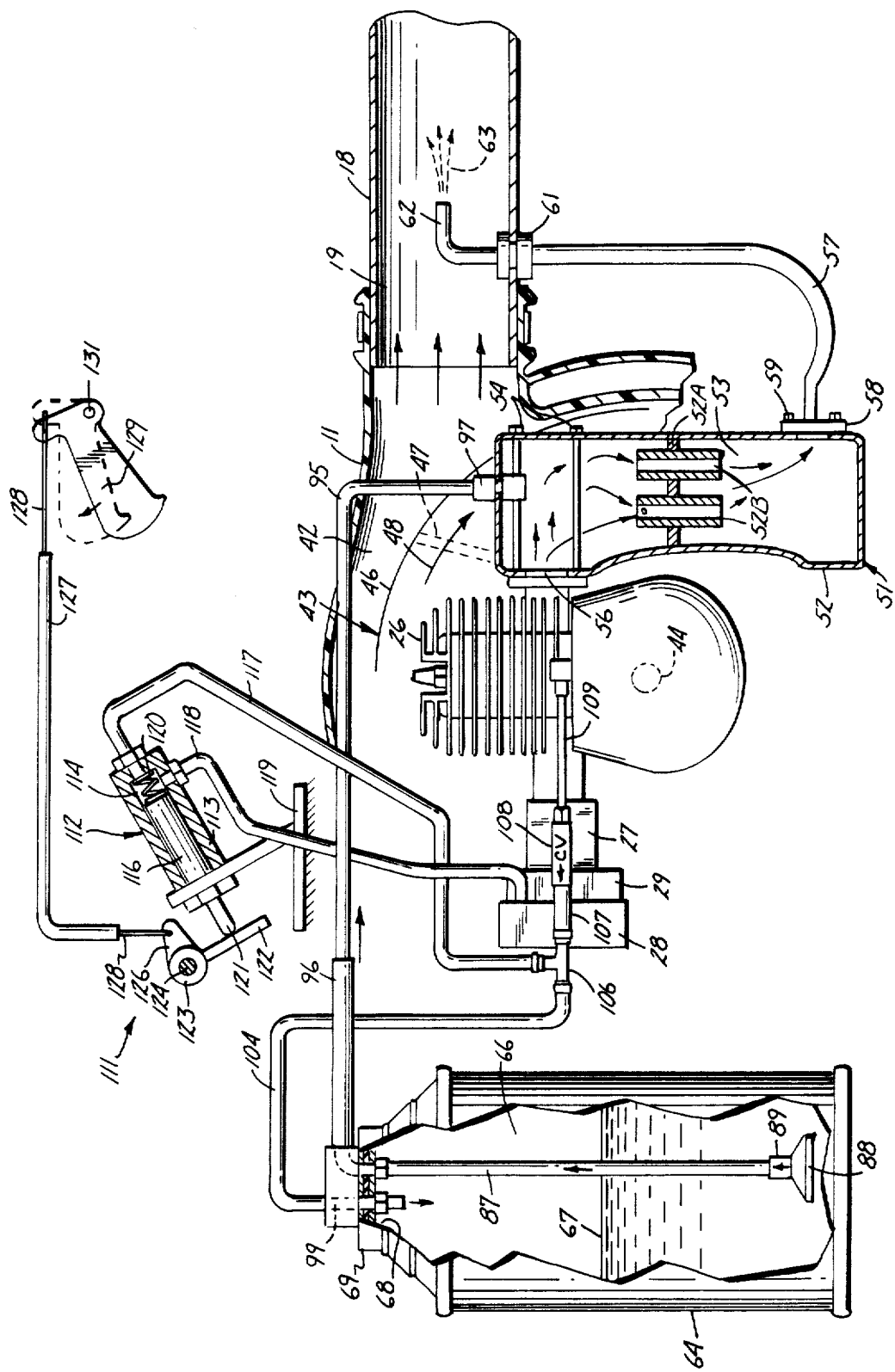
FIG. 10 is a diagram of the fluid control fog generating system of the generator of the invention.

Referring to FIG. 10, a muffler indicated generally at 51 located adjacent internal combustion engine 26 receives the exhaust gases therefrom and a supply of liquid formulation from container 64. Muffler 51 is a permanently sealed structure having a generally rectangular-shaped housing 52 providing a muffler chamber 53. A horizontal baffle plate 52A is located in chamber 53 to attenuate the sound of the combustion process of engine 26. A pair of upright tubes 52B mounted on plate 52A carries the gases, vapors, and atomized liquids to the lower portion of chamber 53. The plate 52A and tubes 52B facilitate the mixing of the hot exhaust gases with the liquid atomized by the high velocity exhaust gases, so as to enhance heat transfer and vaporization of the liquid. A plurality of bolts 54 secure muffler 51 to the exhaust side of internal combustion engine 26 and align the inlet of chamber 53 with engine exhaust outlet 56. A connecting pipe 57 is attached to the outlet end of housing 52. Pipe 57 has a flange 58 accommodating bolts 59 for securing one end of pipe 57 to the outlet of muffler housing 52. The pipe 57 extends upwardly from muffler 51 toward tube 18. A grommet 61 mounted in tube 18 provides a seal for accommodating the upper end of pipe 57. The terminal portion or discharge end 62 of pipe 57 is a tubular member turned in a downstream direction and is located centrally along the longitudinal axis of passage 19. End 62 is open providing a discharge orifice for exhaust gas and atomized and vaporized liquid formulation 63. Pipe 57 and/or end 62 can be a non-metal tubular member, such as a ceramic tube, or a 90-degree bent metal tube covered with suitable heat insulating material (not shown) to minimize condensation of vaporized liquid formulation in pipe 57 and end 62. Insulating material can also protect the operator from the hot connecting pipe 57.

Referring to FIGS. 1, 2, 3, and 5–8, a releasable container 64 is used to store liquid formulation 67, such as CN, CS, or other liquid formulations hereinbefore identified, that are to be dispensed by generator 10. Container 64 has a cylindrical chamber 66 for storing the liquid formulation 67. The top 68 of container 64 accommodates a cylindrical threaded cap 69. Cap 69 is supported on a generally horizontal arm 71. A bolt 72 secures arm 71 to casing 11. A generally vertical bracket 73 extends downwardly from arm 71 and supports a ring 74. The ring 74 surrounds a lower portion of container 64 to protect and support container 64. As shown in FIG. 2, the lower end of bracket 73 is secured with a bolt 76 to casing 11. Container 64 may be removed from cap 69 and from generator 10 by rotating container 64 to disconnect the threaded portion of top 68 from the cap 69. Container 64 is moved in a downward direction to separate it from ring 74 for refilling or replacement with a container full of liquid 67 or another type of liquid.

As shown in FIGS. 5–8, a connector body or mount 77 has a groove 78 along the bottom thereof to accommodate arm 71. Mount 77 engages the top of cap 69. Body 77 has a first passage 79 that accommodates an upright tubular bolt 81. As shown in FIG. 6, bolt 81 extends upwardly through cap 69 and a hole 82 in arm 71 and is threaded into body 77. Bolt 81 has a hex head 83 on the lower end thereof and an extension which is inserted into the upper end of dip tube 87. A sealing gasket 84 and rigid disc 86 are interposed between hex head 83 and the lower horizontal surface of cap 69. As shown in FIGS. 5 and 10, the elongated pickup pipe or dip tube 87 extends downwardly from hex head 83 to a position closely adjacent the bottom of cohtainer 64. A strainer 88 is mounted on the lower end of pipe 87 to filter the liquid formulation that is moved up pipe 87. A one-way valve or check valve 89 is secured to the lower end of pickup pipe 87. Valve 89 allows the liquid formulation to move up pipe 87 and blocks reverse flow of liquid formulation from pipe 87 back into container chamber 66. Strainer 88 and/or the check valve may be omitted, if desired.

Referring to FIG. 6, the rate of flow of liquid formulation from container 64 is controlled by a flow restrictor or plug 91 having a suitable orifice or passage 92. The flow restrictor 91 is retained in the end of nipple 93 by a press fit. Connector nipple 93 has a passage 94 for carrying the liquid formulation to a plastic or rubber hose 96. Hose 96 is mounted on connector nipple 93 and extends to metal tube 95 connected to the top of muffler housing 52. As shown in FIG. 10, a connector 97 secures the discharge end of tube 95 to the top of muffler housing 52. The liquid formulation carried by tube 95 and hose 96 is discharged into the top of muffler chamber 53 adjacent the top of engine exhaust outlet 56. The high velocity exhaust gases atomize the liquid formulations. Vaporization is facilitated by mixing of the hot exhaust gas with the atomized liquid formulation. Vaporization is also facilitated by the baffle 52A and interconnecting tubes 52B.

As shown in FIGS. 7 and 8, body 77 has a second passage 98 accommodating a second hollow or tubular bolt 99. Bolt 99 extends upwardly through cap 69, a hole 101 in arm 71, and threads into body 77. A hex head 102 on the lower end of hollow bolt 99 bears against metal disc 86. Bolt 99 provides a passage for crankcase gases under pressure into container chamber 66. As shown in FIG. 7, a nipple connector 103 threaded into body 77 provides a passage for connecting passage 98 to a hose 104. As shown in FIG. 10, hose 104 is connected to a T-connector or member 106. A short hose 107, check valve 108, and metal pipe 109, connect T-connector 106 to the crankcase scavenge pumping portion of the two cycle internal combustion engine 26. Engine 26 has a crankcase that is under pressure during the power stroke of the engine. Check valve 108 prevents reverse flow of gas pressure back to the crankcase when the piston moves upward on the compression stroke of the engine. This insures that the gas pressure in container chamber 66 approaches the peak crankcase gas pressure. Pipe 109 is open to the crankcase so that the gases under pressure in the engine crankcase are delivered to the top of the chamber 66 of container 64. This places gas pressure on liquid formulation 67 forcing the liquid formulation upwardly through the check valve 89, pickup pipe 87, hose 96, and tube 95 into the top of muffler chamber 53. The high velocity hot exhaust gas flowing from engine exhaust outlet 56 into muffler chamber 53 first atomizes and then vaporizes the liquid formulation. The mixture of vaporized liquid formulation and exhaust gas is carried by connecting pipe 57 and discharged as a continuous stream of vapor and gas, shown by arrow 63 in FIG. 10, into the air being moved through the passage 19 of tube 18. In addition to vapors, liquid may also issue from pipe end 62 in the form of finely atomized liquid droplets sheared by engine exhaust velocity, and also in the form of finely atomized droplets sheared from the pipe end 62 by the high velocity flow of air into tube 18. The air flowing in passage 19 carries the vapor and gases into the atmosphere. Mixing with the cool air causes condensation of the vapor into condensation particles forming a fog. The fog is carried by the stream of air discharged from tube 18 away from the operator to the desired location or target area.

A control system indicated generally at 111 in FIG. 10 is used to regulate the flow of gases under pressure from the crankcase of the internal combustion engine 26 to container chamber 66 and thereby control the flow of liquid formulation from container 64 to muffler 51. Control system 111 is operable to selectively start and stop the flow of liquid formulation to muffler 51 without stopping engine 26. Control system 111 has a valve unit 112 operable to normally vent the gases under pressure to engine intake air filter 28. Valve unit 112 may be moved to a closed position by the operator, whereby gas pressure from the crankcase of the internal combustion engine 26 is directed to the top of container chamber 66. This gas pressure forces liquid formulation 67 up pipe 87 into hose 96 and tube 95 connected to the top of muffler 51. As long as valve unit 112 is closed, liquid formulation will be supplied to muffler 51. When valve unit 112 is open the gases under pressure pumped from engine 26 are vented to engine intake air filter unit 28. Some of the gases under pressure in container chamber 66 are also vented to engine air filter unit 28 through open valve unit 112. The release of gas pressure in container 64, in combination with back pressure from muffler 51, promptly stops the flow of fluid in line 96 and tube 95.

Valve unit 112 has a body or cylinder 113 provided with a longitudinal bore 114. A piston 116 reciprocates in bore 114 between a first open position and a second closed position to control the flow of gas from engine 26 to intake air filter unit 28 or container 64. A compression coil spring 120 biases piston 116 to a first position to open valve unit 112. A first hose 117 connects the T-connector 106 to the end of the valve cylinder 113. A second hose 118 connects a side of cylinder 113 to the intake air filter unit 28. An angled bracket 119 mounts the valve unit 112 on the top of carburetor 27.

Valve unit 112 has an external push rod actuator 121 engageable with a first arm 122. Arm 122 is secured to a sleeve 123 rotatably mounted on a pivot member or pin 124. Pin 124 is mounted on internal wall 24. A second arm 126 secured to rotatable sleeve 123 is moved by means of flexible cable assembly 127. Cable assembly 127 includes a movable wire 128 connected to second arm 126 at one end and to a trigger 129 at the other end thereof. A pivot pin 131 mounts trigger 129 on the lower side of the forward portion of handle 23. When trigger 129 is pulled in an upward direction, wire 128 is moved to rotate arms 122 and 126 in a counterclockwise direction, as seen in FIG. 10. This moves piston 116 upwardly into bore 114 against the biasing force of spring 120 to a closed position. As long as trigger 129 is in an upward or squeezed position, the gases under pressure from the internal combustion engine crankcase will pressurize container 64 through hose 104. When trigger 129 is released, spring 120 immediately moves piston 116 back to the first position opening valve unit 112. Thus, control system 111 controls the crankcase gases under pressure to container 64 so as to selectively turn on or off the flow of liquid formulation to muffler 51. The liquid formulation 67 does not come in contact with valve unit 112, nor the crankcase gases pressure lines connecting valve unit 112 with crankcase of engine 26 and container 64. There are no moving parts exposed to the liquid formulation. Thus, the liquid formulation cannot corrode, nor gum up, or otherwise render the valve unit 112 inoperative.

In use, engine 26 is started by moving switch button 41 to its on or run position and pulling handle 39 of recoil starter unit 38. Choke lever 31 can be used as a cold engine starting aid. Normally, engine 26 is operated at full speed to provide maximum exhaust gas heat, as well as maximum air flow through passage 19 of tube 18. The torque required to rotate blower 43 serves to load the engine 26 so that it is operated at substantially full power output. This insures maximum exhaust gas heat output to muffler 51 for the purpose of vaporizing the liquid formulation introduced in muffler 51. Fog and smoke will not be discharged until trigger 129 is pulled up or squeezed.

Generator 10 is carried by the operator with one hand grasping handle 23. The first finger of the hand is used to pull trigger 129. When trigger 129 is pulled up or in the dotted position, as shown in FIG. 10, it pulls wire 128 and rotates crank arms 122 and 126. Arm 122 is engageable with push rod actuator 121 and moves piston 116 in an upward direction to close valve unit 112. Valve unit 112 will remain closed as long as trigger 129 is held in the up position. The gas pressure generated in the engine crankcase 26 is transmitted through check valve 108 and hose 104 into the top of container chamber 66. Check valve 108 insures that the gas pressure in container chamber 66 approaches the peak cyclic crankcase gas pressure, as it prevents the reverse flow of the gas pressure in hoses 104 and 107. The gas pressure in container chamber 66 forces liquid formulation 67 up pickup tube 87. As shown in FIG. 6, plug 91, having the restriction orifice 92, regulates the rate of flow of the liquid formulation through connector body 77 into hose 96. The size of orifice 92 can be changed to accommodate different types and viscosities of liquid formulations.

The liquid formulations flow through hose 96 and tube 95 into the top of muffler 51. As shown in FIG. 10, the high velocity hot exhaust gas from engine 26 atomizes and mixes with the liquid formulation causing vaporization of liquid formulation in muffler chamber 53. Baffle 52A and tubes 52B in muffler 51 facilitate mixing of liquid particles with the hot exhaust gases and vaporization of the liquid particles. The exhaust gases and atomized and/or vaporized liquid formulations are carried via connecting pipe 57 to tubular end 62. The exhaust gases and atomized and/or vaporized liquid formulations are discharged into the air flowing in passage 19. The blower 43, being operated by the engine 26, establishes a continuous flow of high velocity air, which is directed through passage 19 and discharged through the open end 21 of tube 18 into the atmosphere. The hot exhaust gases and atomized and/or vaporized liquid formulations are mixed with the air in passage 19. The cool air in passage 19 and in the atmosphere at the open end of tube 18 causes condensation of the vaporized liquid formulations into tiny particles forming a visible fog. For example, the condensation particles may have a diameter of 1 micron or less.

Tubular end 62 is located generally along the central axis of passage 19 and discharges the exhaust gas and atomized and/ or vaporized liquid formulations in a downstream direction. The high velocity air flowing in passage 19 surrounds the discharged exhaust gas and atomized and/or vaporized liquid formulations and provides a flowing annular sheath of air that carries the exhaust gas and atomized and/or vaporized liquid formulations into the atmosphere. Tubular end 62 is located inwardly from open end 21 a distance so that the expanding conical stream of materials, shown in broken lines in FIG. 4, issuing from tubular end 62 does not substantially contact the wall of tube 18. The flowing annular sheath of air in passage 19 inhibits condensation and collection of the liquid formulations on the inside surface of tube 18. Any liquid formulations collected in liquid state on tube 18 will be picked up by the flowing air and atomized by the rapid moving air. The sheath of air also minimizes the transfer of heat from the hot exhaust gases to tube 18. The fog will continue to be carried by the air discharged from tube 18 in a direction away from the operator. The distance that the fog and air is propelled away from the operator is a function of the speed of engine 26. For example, engine 26 running at full throttle can propel the air and fog at approximately 12 meters in front of tube 18.

When trigger 129 is released, piston 116 will move to its open position. This movement is caused by the force of spring 120 engageable with piston 116. The pressure of the gases in line 117 also facilitates the movement of piston 116 to the open position. When piston 116 is in the open position, as shown in FIG. 10, the gases under pressure from the crankcase of internal combustion engine 26 will be diverted via T-member 106, line 117, and line 118 to the engine air filter unit 28. The gas pressure in the container chamber 66 will be immediately reduced. The gas pressure in container chamber 66 will flow in a reverse direction through hose 104 into hose 117 leading to the valve unit 112. The release of the gas pressure in container chamber 66 stops the flow of liquid formulation of pickup tube 87 into hose 96. There is an abrupt shut-off of the liquid formulation flow in hose 96 and tube 95 due to the exhaust gas back pressure in muffler chamber 53. This prevents the further discharge of the liquid formulation in hose 96 and tube 95 into muffler 51. As soon as trigger 129 is released, the dispensing of liquid formulation into the muffler 51 is terminated, thereby stopping the atomization and vaporization of liquid formulation. The hot exhaust gas from engine 26 purges the muffler 51 and connecting pipe 57. The generation of the fog is promptly terminated.

While there has been shown and described an embodiment of a blower type thermal fog and smoke generator having a fog control system, it is understood that changes and modifications may be made by those skilled in the art without departing from the invention. The invention is defined in the following claims.

The embodiments of the invention in which an exclusive property or privilege is claimed are defined as follows:

1. An apparatus for producing and dispensing fog, smoke, mist, and the like, comprising: a housing having a chamber, an air inlet opening allowing air to flow into the chamber, and tube means having an air discharge passage open to the chamber to carry air from the chamber to the atmosphere, an internal combustion engine mounted on the housing operable to produce hot exhaust gas and a supply of crankcase gases under pressure, blower means located in the chamber drivably connected to the engine operable to load the engine and move air through the chamber and air discharge passage and dispense air into the atmosphere, means for carrying the hot exhaust gas from the engine to the tube means and discharging said hot exhaust gas into the air discharge passage, container means for storing a liquid formulation, means mounting the container means on the housing, line means for carrying the liquid formulation from the container means to the means for carrying the hot exhaust gas, and control means for selectively supplying said crankcase gases under pressure from said engine to said container means, said crankcase gases under pressure in the container means forcing said liquid formulation from said container means and through said line means into the means for carrying the hot exhaust gas, the velocity of said exhaust gas atomizing said liquid formulation and the heat of said hot exhaust gas vaporizing at least part of said atomized liquid formulation, said atomized and vaporized liquid formulation being discharged into said air discharge passage, mixed with the air flowing in said passage, and dispensed into the atmosphere, said vaporized liquid formulation being condensed by the cool air forming a fog, smoke, or the like, said control means having means operable to vent the crankcase gases under pressure from the container means to reduce the pressure of the crankcase in the container means to terminate the flow of liquid formulation to the means for carrying the hot exhaust gas from the engine.

2. The apparatus of claim 1 wherein: the means for carrying the hot exhaust gas and atomized and vaporized liquid formulation from the engine to the tube means includes a muffler having a chamber for receiving the hot exhaust gas from the engine and tubular means for carrying the exhaust gas and atomized and vaporized liquid formulation from the muffler to said air discharge passage, said line means being connected to the muffler whereby said liquid formulation is discharged into the chamber of the muffler.

3. The apparatus of claim 2 wherein: said muffler has at least one baffle in said chamber of the muffler and opening means through the baffle means allowing exhaust gas and atomized and vaporized liquid formulation to flow through said chamber.

4. The apparatus of claim 2 wherein: said tubular means has an end portion having a discharge opening, said end portion being extended generally along the longitudinal axis of the air passage of the tube means.

5. The apparatus of claim 4 wherein: said end portion has a linear tubular member located along the longitudinal axis of the air passage of the tube means, said tubular member being located adjacent the inlet portion of said air passage and having a downstream end with said gas discharge opening therein whereby liquid formulation collected on the tubular member is atomized by the air moving in said air passage.

6. The apparatus of claim 1 wherein: the means mounting the container means on the housing includes a cap, said cap and container means having cooperating means for releasably holding the container means in assembled relation with the cap.

7. The apparatus of claim 6 including: a body having a passage for carrying liquid formulation means connecting the cap to the body, and a tube mounted on the cap and body and extended into the container for carrying liquid formulation from the container chamber to the passage in the body, said line means being connected to the body for carrying liquid formulation to said means for carrying the hot exhaust gas.

8. The apparatus of claim 7 including: means located in the passage of the body for controlling the rate of flow of liquid formulation into the line means.

9. The apparatus of claim 8 wherein: said means located in the passage of the body comprises a plug having-a hole for restricting the rate of flow of liquid formulation to the line means.

10. The apparatus of claim 7 including: one-way valve means connected to the tube operable to allow liquid formulation to flow from the container means to the line means.

11. An apparatus for producing and dispensing fog, smoke, mist, and the like, comprising: a housing having a chamber, an air inlet opening allowing air to flow into the chamber, and tube means having an air discharge passage open to the chamber to carry air from the chamber to the atmosphere, an internal combustion engine mounted on the housing operable to produce hot exhaust gas and a supply of crankcase gases under pressure, blower means located in the chamber drivably connected to the engine operable to load the engine and move air through the chamber and air discharge passage and dispense air into the atmosphere, means for carrying the hot exhaust gas from the engine to the tube means and discharging said hot exhaust gas into the air discharge passage, container means for storing a liquid formulation, means mounting the container means on the housing, line means for carrying the liquid formulation from the container means to the means for carrying the hot exhaust gas, and control means for selectively supplying said crankcase gases under pressure from said engine to said container means, said crankcase gases under pressure in the container means forcing said liquid formulation from said container means and through said line means into the means for carrying the hot exhaust gas, the velocity of said exhaust gas atomizing said liquid formulation and the heat of said hot exhaust gas vaporizing at least part of said atomized liquid formulation, said atomized and vaporized liquid formulation being discharged into said air discharge passage, mixed with the air flowing in said passage, and dispensed into the atmosphere, said vaporized liquid formulation being condensed by the cool air forming a fog, smoke, or the like, said control means includes second line means for carrying crankcase gases under pressure from the engine to the container chamber, and means connected to the second line means selectively operable to vent the crankcase gases under pressure in the second line means to atmosphere, thereby reducing the pressure of the crankcase gases in the container chamber to terminate the flow of liquid formulation to the means for carrying the hot exhaust gas from the engine.

12. The apparatus of claim 11 wherein: the means connected to the second line means includes a valve unit having an open position allowing the gases under pressure to vent to atmosphere and a closed position to prevent venting of the gases to atmosphere.

13. The apparatus of claim 12 including: hand-operated means for selectively operating the valve unit to its closed position and biasing means for moving the valve unit to its open position.

14. The apparatus of claim 13 including: a handle attached to the housing, said hand-operated means having a movable trigger mounted on the handle, and means operably connecting the trigger to the valve unit whereby, on movement of the trigger, the valve unit is moved to the closed position.

15. The apparatus of claim 11 including: one-way valve means located in said second line means allowing crankcase gases to flow from the engine to the container means.

16. The apparatus of claim 11 wherein: the engine has air intake means, said crankcase gases being vented to said air intake means.

17. The apparatus of claim 11 wherein: the engine has air intake means, said control means includes second line means for carrying crankcase gases under pressure from the engine to the container chamber, a valve unit connected to the second line means, third line means connecting the valve unit to the air intake means, said valve unit having an open position allowing the crankcase gases under pressure to vent through the third line means to the air intake means and a closed position to prevent venting of the crankcase gases to the air intake means.

18. The apparatus of claim 17 including: hand-operated means for selectively operating the valve unit to its closed position and biasing means for moving the valve unit to its open position.

19. The apparatus of claim 17 including: one-way valve means located in said second line means allowing crankcase gases to flow from the engine to the container means.

20. The apparatus of claim 11 wherein: the means for carrying the hot exhaust gas from the engine includes a muffler having at least one chamber and an outlet, and an exhaust pipe connecting the muffler outlet to the tube means, said line means being connected to the muffler to discharge the liquid formulation into the chamber of the muffler.

21. The apparatus of claim 20 wherein: said muffler has an inlet end and an outlet end, said hot exhaust being discharged from the engine into the inlet end of the muffler, said line means being connected to the muffler adjacent the inlet end thereof, said exhaust pipe being connected to the outlet end of the muffler.

22. The apparatus of claim 21 wherein: said muffler has at least one baffle separating the chamber of the muffler into an inlet chamber section and an outlet chamber section, and opening means having at least one passage through the baffle allowing exhaust gas and atomized and vaporized liquid formulation to flow from the inlet chamber section to the outlet chamber section.

23. The apparatus of claim 20 wherein: said exhaust pipe has an end portion having an exhaust gas discharge opening, said opening having a flow axis extended in the direction of the flow of air in the tube means, said end portion being located generally along the longitudinal axis of the air passage of the tube means.

24. The apparatus of claim 23 wherein: said end portion has a linear tubular member located along the longitudinal axis of the air passage of the tube means, said tubular member having a downstream end located adjacent the inlet portion of said air passage, and said exhaust gas discharge opening being in the downstream end of the tubular member.

25. The apparatus of claim 11 including: liquid formulation flow restrictor means associated with the line means to regulate the rate of flow of liquid formulation from the container means to the means for carrying the hot exhaust gas from the engine.

26. An apparatus for producing and dispensing fog, smoke, mist, and the like, comprising: an internal combustion engine operable to produce hot exhaust first gas and a supply of second gases under pressure, means for loading the engine whereby the load absorbed is substantially the maximum power output of the engine so that the engine produces said hot exhaust first gas, means for carrying the first gas from the engine to the atmosphere, container means having a chamber for storing a liquid formulation, line means for carrying the liquid formulation from the container means to the means for carrying the first gas, and control means for selectively supplying said second gas under pressure to said container means or venting the second gas to atmosphere, said second gas under pressure forcing said liquid formulation from said container means and through said line means into the means for carrying the first gas, the velocity of said first gas atomizing said liquid formulation and the heat of said first gas vaporizing at least part of said atomized liquid formulation, said atomized and vaporized liquid formulation being discharged into the atmosphere, and said vaporized part of the liquid formulation condensed by atmosphere air forming a fog, smoke, or the like, said control means having means operable to vent the second gas from the container means to reduce the pressure of the second gas in the container means to terminate the flow of liquid formulation from said container means to the means for carrying the first gas.

27. The apparatus of claim 26 wherein: the means for carrying the hot exhaust first gas from the engine to the atmosphere includes a muffler having at least one chamber for receiving the hot exhaust first gas from the engine and an exhaust pipe connected to the muffler for carrying the first exhaust gas and atomized and vaporized liquid formulation, said line means being connected to the muffler whereby said liquid formulation is discharged into the chamber of the muffler.

28. An apparatus for producing and dispensing fog, smoke, mist and the like comprising: an internal combustion engine operable to produce hot exhaust first gas and a supply of second gases under pressure, means for loading the engine whereby the load absorbed is substantially the maximum power output of the engine so that the engine produces said hot exhaust first gas, means for carrying the first gas from the engine to the atmosphere, container means having a chamber for storing a liquid formulation, line means for carrying the liquid formulation from the container means to the means for carrying the first gas, and control means for selectively supplying said second gas under pressure to said container means or venting the second gas to atmosphere, said second gas under pressure forcing said liquid formulation form said container means and through said line means into the means for carrying first gas, the velocity of said first gas atomizing said liquid formulation and the heat of said first gas vaporizing at least a part of said atomized liquid formulation, said atomized and vaporized liquid formulation being discharged into the atmosphere, and said vaporized part of said liquid formulation condensed by atmosphere air forming a fog, smoke, or the like, said means for carrying the hot exhaust first gas from the engine to the atmosphere includes a muffler having at least one chamber for receiving the hot exhaust first gas from the engine and an exhaust pipe connected to the muffler for carrying the first exhaust gas and atomized and vaporized liquid formulation, said line means being connected to the muffler, whereby said liquid formulation is discharged into the chamber of the muffler, said muffler having at least one baffle located in said chamber, and opening means associated with the baffle to allow said exhaust first gas and atomized and vaporized liquid formulation to flow through said chamber, said exhaust first gas pressure in the chamber being operable to stop the flow of liquid formulation to the muffler when the control means vents the second gas to atmosphere.

29. The apparatus of claim 28 wherein: the means for loading the engine includes blower means having an air outlet passage operable to move air through said air outlet passage into the atmosphere, said exhaust pipe having an end portion located in said outlet passage and an outlet opening to discharge exhaust first gas and atomized and vaporized liquid formulation into the air flowing in said outlet passage.

30. The apparatus of claim 29 wherein: said end portion is located generally along the longitudinal axis of said air outlet passage.

31. The apparatus of claim 30 wherein: said end portion has a linear tubular member located along the longitudinal axis of said air outlet passage, said tubular member having a downstream end, said outlet opening being in the downstream end of the tubular member whereby liquid formulation collected on the tubular member is atomized by the air moving in the air outlet passage.

32. An apparatus for producing and dispensing fog, smoke, mist, and the like, comprising: an internal combustion engine operable to produce hot exhaust first gas and a supply of second gases under pressure, means for loading the engine whereby the load absorbed is substantially the maximum power output of the engine so that the engine produces said hot exhaust first gas, means for carrying the first gas from the engine to the atmosphere, container means having a chamber for storing a liquid formulation, line means for carrying the liquid formulation from the container means to the means for carrying the first gas, and control means for selectively supplying said second gas under pressure to said container means or venting the second gas to atmosphere, said second gas under pressure forcing said liquid formulation from said container means and through said line means into the means for carrying the first gas, the velocity of said first gas atomizing said liquid formulation and the heat of said first gas vaporizing at least part of said atomized liquid formulation, said atomized and vaporized liquid formulation being discharged into the atmosphere, and said vaporized part of the liquid formulation condensed by atmosphere air forming a fog, smoke, or the like, said control means includes second line means for carrying the second gas under pressure from the engine to the container chamber, and means connected to the second line means selectively operable to vent the second gas under pressure in the second line means to atmosphere, thereby reducing the pressure of the second gas in the container chamber to terminate the flow of liquid formulation to the means for carrying the hot exhaust gas from the engine.

33. The apparatus of claim 32 including: one-way valve means located in said second line means allowing the second gas to flow to the container means.

34. The apparatus of claim 32 wherein: the engine has air intake means, said second gas being vented to said air intake means.

35. The apparatus of claim 32 wherein: the engine has air intake means, said control means includes second line means for carrying the second gas under pressure to the container chamber, a valve unit connected to the second line means, third line means connecting the valve unit to the air intake means, said valve unit having an open position allowing the second gas under pressure to vent through the third line means to the air intake means and a closed position to prevent venting of the second gas to the air intake means.

36. The apparatus of claim 35 including: hand-operated means for selectively operating the valve unit to its closed position and biasing means for moving the valve unit to its open position.

37. The apparatus of claim 35 including: one-way valve means located in said second line means allowing crankcase gases to flow from the engine to the container means.

38. The apparatus of claim 32 wherein: the means connected to the second line means includes a valve unit having an open position allowing the second gas under pressure to vent to atmosphere and a closed position to prevent venting of the second gas to atmosphere.

39. The apparatus of claim 38 including: hand-operated means for selectively operating the valve unit to its open and closed positions.

40. The apparatus of claim 39 wherein: the hand-operated means includes a movable trigger and means connecting the trigger to the valve unit whereby, on movement of the trigger, the valve unit is moved to the closed position, and biasing means associated with the valve unit to bias the valve unit to the open position.

41. The apparatus of claim 32 including: liquid formulation flow restrictor means associated with the line means to regulate the rate of flow of liquid formulation from the container means to the means for carrying the hot exhaust first gas from the engine.

42. The apparatus of claim 1 wherein: the means operable to vent the crankcase gases includes a valve unit having an open position allowing the crankcase gases under pressure to vent to atmosphere and a closed position to prevent venting of the crankcase gases to atmosphere.

43. The apparatus of claim 42 including: hand-operated means for selectively operating the valve unit to its closed position and biasing means for moving the valve unit to its open position.

44. The apparatus of claim 43 including: handle means attached to the housing, said hand-operated means having a movable trigger mounted on the handle means, and means operably connecting the trigger to the valve unit whereby on movement of the trigger, the valve unit is moved to the closed position.

45. The apparatus of claim 1 including: one-way valve means allowing crankcase gases to flow from the engine to the container means.

46. The apparatus of claim 1 wherein: the engine has air intake means, said crankcase gases being vented to said air intake means.

47. The apparatus of claim 1 wherein: the means for carrying the hot gas from the engine includes a muffler having at least one chamber and an outlet, and an exhaust pipe connecting the muffler outlet to the tube means, said line means being connected to the muffler to discharge the liquid formulation into the chamber of the muffler.

48. The apparatus of claim 47 wherein: said muffler has at least one baffle separating the chamber of the muffler to an inlet chamber section and an outlet chamber section, and an opening means having at least one passage through the baffle allowing exhaust gas and atomized and vaporized liquid formulation to flow from the inlet chamber section to the outlet chamber section.

49. The apparatus of claim 1 including: liquid formulation flow restrictor means associated with the line means to regulate the flow of liquid formulation form the container means to the means for carrying the hot exhaust gas from the engine.

50. The apparatus of claim 26 wherein: the means for loading the engine includes blower means having an air outlet passage operable to move air through said air outlet passage into the atmosphere, said exhaust pipe having an end portion located in said outlet passage and an outlet opening to discharge first gas and an atomized and vaporized liquid formulation into the air flowing in said outlet passage.

51. The apparatus of claim 50 wherein: said end portion is located generally along the longitudinal axis of said air outlet passage.

52. The apparatus of claim 26 including: one-way valve means allowing the second gas to flow to the container means.

53. The apparatus of claim 26 wherein: the engine has air intake means, said second gas being vented to said air intake means.

54. The apparatus of claim 26 wherein: said means operable to vent the second gases from the container means includes a valve unit having an open position allowing the second gases under pressure to vent to the atmosphere and a closed position to prevent venting of the second gases to the atmosphere.

55. The apparatus of claim 54 including: hand-operated means for selectively operating said valve unit to its closed position and biasing means for moving the valve unit to its open position.

56. The apparatus of claim 26 including: liquid formulation flow restrictor means associated with said line means to regulate the rate of flow of liquid formulation from the container means to the means for carrying the hot exhaust first gas from the engine.

* * * * *